United States Patent
Witte et al.

(10) Patent No.: US 10,143,634 B2
(45) Date of Patent: Dec. 4, 2018

(54) THICKENING DEVELOPER FOR OXIDATION DYES

(71) Applicant: Henkel AG & Co. KGaA, Duesseldorf (DE)

(72) Inventors: Christiane Witte, Hetlingen (DE); Stephan Schwartz, Wedel (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 15/622,763

(22) Filed: Jun. 14, 2017

(65) Prior Publication Data

US 2017/0273879 A1 Sep. 28, 2017

Related U.S. Application Data

(63) Continuation of application No. PCT/EP2015/075084, filed on Oct. 29, 2015.

(30) Foreign Application Priority Data

Dec. 19, 2014 (DE) .................. 10 2014 226 540

(51) Int. Cl.
| | |
|---|---|
| *A61Q 5/10* | (2006.01) |
| *A61K 8/22* | (2006.01) |
| *A61K 8/37* | (2006.01) |
| *A61Q 5/06* | (2006.01) |
| *A61K 8/06* | (2006.01) |
| *A61K 8/34* | (2006.01) |

(52) U.S. Cl.
CPC .............. *A61K 8/22* (2013.01); *A61K 8/062* (2013.01); *A61K 8/34* (2013.01); *A61K 8/375* (2013.01); *A61Q 5/06* (2013.01); *A61Q 5/10* (2013.01); *A61K 2800/4324* (2013.01); *A61K 2800/882* (2013.01)

(58) Field of Classification Search
CPC . A61K 8/22; A61K 8/375; A61K 8/34; A61K 8/062; A61K 2800/882; A61K 2800/4324; A61Q 5/10
See application file for complete search history.

(56) References Cited

U.S. PATENT DOCUMENTS

| | | | |
|---|---|---|---|
| 8,840,682 B2 * | 9/2014 | Pratt | A61K 8/19 8/101 |
| 2010/0000029 A1 * | 1/2010 | Eliu | A61K 8/4946 8/428 |
| 2013/0205515 A1 * | 8/2013 | Misu | A61K 8/411 8/401 |
| 2015/0272845 A1 | 10/2015 | Neuba et al. | |

FOREIGN PATENT DOCUMENTS

| | | |
|---|---|---|
| EP | 2006134051 A1 | 12/2006 |
| WO | 2012032671 A1 | 3/2012 |

OTHER PUBLICATIONS

STIC Search Report dated Aug. 10, 2017.*
PCT International Search Report (PCT/EP2015/075084) dated Apr. 12, 2015.
Anonymous: "GNPD—Cream Colouration Kit", Oct. 1, 2008 (Oct. 1, 2008), XP055231766, Gefunden im Internet: UR. http://www.gnpd.com/sinatra/recordpage/982880/from_search/wOil0KHxSH/ [gefunden am Nov. 26, 2015] das ganze Dokument.

\* cited by examiner

*Primary Examiner* — Eisa B Elhilo
(74) *Attorney, Agent, or Firm* — P. Scott Smith

(57) ABSTRACT

A composition for oxidative hair treatment, containing 50-96% by weight; 0.5-20% by weight hydrogen peroxide; at least one polyethylene glycol ether of a monoester of glycerol and a C12-C22 carboxylic acid having 110-500 ethylene oxide units in the molecule, according to formula (I), wherein the sum of the indices x+y+z stands for a number in the range of 110 to 500, and R stands for an alkyl functional group having 11 to 21 carbon atoms, which may be saturated or unsaturated, linear or branched, wherein all stated quantities are based on the weight of the oxidation composition. Wherein the composition is suited for use as a developer for oxidative hair lighteners and/or hair dyes. The alkaline composition (A) is present as an oil-in-water emulsion and includes at least one alkalizing agent, and has a pH in the range of 8 to 11.5.

13 Claims, No Drawings

THICKENING DEVELOPER FOR OXIDATION DYES

FIELD OF THE INVENTION

The present patent application relates to compositions that are suitable as oxidizing agents for emulsion-type, in particular cream-type, hair lightening and/or hair dyeing preparations, the emulsion-type hair lightening and/or hair dyeing preparations preferably being present in the form of an oil-in-water emulsion and containing at least one alkalizing agent and optionally at least one oxidation dye precursor, and having a pH in the range of 8 to 11.5, measured at 20° C., and with which the application properties of the application mixture, such as dispersion stability and drop behavior of the mixture and retention of the mixture on the hair, as well as skin and scalp tolerability may be markedly improved.

BACKGROUND OF THE INVENTION

A further subject matter of the present patent invention relates to agents for changing the color of keratinic fibers, the agents being producible from two separate compositions by mixing the two compositions together, wherein one of the two compositions is an oxidative composition according to the first subject matter of the patent application, and the second composition is a hair lightening and/or hair dyeing preparation that is present in the form of an oil-in-water emulsion and includes at least one alkalizing agent and optionally at least one oxidation dye precursor and has a pH in the range of 8 to 11.5, measured at 20° C., and in addition preferably includes, in each case based on its weight, 50-80% by weight water, more preferably 5-20% by weight, particularly preferably 8-15% by weight, of at least one fatty component having a melting point in the range of 28-80° C., and which is preferably selected from linear saturated 1-alkanols having 12-30 carbon atoms, and esters of monohydric and polyhydric C1-C10 alkanols and C8-C30 alkanoic acids and mixtures thereof, also preferably at least one nonionic and/or anionic surfactant in a total quantity of 1-8% by weight, preferably 2-6% by weight.

A further subject matter of the present patent invention relates to a kit for oxidatively changing the color of keratinic fibers, comprising an emulsion-type, optionally dye-containing, alkaline preparation and an aqueous hydrogen peroxide preparation, the hydrogen peroxide preparation being optimized in such a way that that the ready-to-use mixture composed of an alkaline emulsion and a hydrogen peroxide preparation is a viscous cream or paste having a viscosity in the range of 5000 to 15,000 mPas (for example, measured at 20° C. with a Haake Model MV2 viscometer at a speed of 8 rpm), and which may be easily applied to the fibers to be lightened and/or dyed, and remains there during the application period of 5 to 60 minutes without prematurely dripping from the hair in significant quantities.

A further subject matter of the present patent invention relates to a method for oxidatively changing the color of keratinic fibers, the ready-to-apply lightening and/or dyeing agent being prepared by mixing the components of the above-mentioned kit immediately before use, then applied to the fibers, in particular hair, and rinsed off after an exposure time of 5 to 60 minutes.

The present invention relates to the oxidative changing of the color of keratinic fibers, in particular hair. Since during the treatment of keratinic fibers, in particular hair, with oxidizing agents, in particular hydrogen peroxide, the fiber's own dye, melanin, is destroyed to a certain degree, the fibers/hair are/is necessarily lightened; i.e., their/its color change(s) even without the presence of a dye. Therefore, the term "changing of the color" within the meaning of the present patent invention encompasses lightening as well as dyeing with one or more dyes.

Those skilled in the art are familiar with various methods for changing the color of human hair. In general, either substantive dyes or oxidation dyes, which result from oxidative coupling of one or more developer components with one another or with one or more coupler components, are used for dyeing human hair. Coupler components and developer components are also referred to as oxidation dye precursors. The colorings achieved using oxidation dyes are usually referred to as permanent or semipermanent colorings.

These agents usually contain hydrogen peroxide as oxidizing agent. Since hydrogen peroxide has unsatisfactory storage stability in the alkaline pH range, oxidative dyes are typically composed of two components that are mixed together immediately before use. The one component includes hydrogen peroxide in aqueous solution or emulsion, this composition having an acidic pH in the range of 2.5 to 5.5 for stabilizing the hydrogen peroxide. The second component includes one or more alkalizing agents in a quantity such that the application mixture composed of both components has a pH in the range of 8 to 11. If the alkaline preparation includes no dye or only small quantities of dye, the latter being used for covering up undesirable tints that may arise during the melanin oxidation, the alkaline preparation is a lightening or bleaching agent. However, the alkaline preparation may also contain oxidation dye precursors and/or substantive dyes; the resulting application mixture is then used as a coloring agent. In addition, there are dye kits and dyeing methods in which the application mixture composed of both components has a pH in the range of approximately 6 to 7.9; however, the color results of these so-called "acidic" colorings often do not attain the quality that is achieved with alkaline application mixtures.

For oxidatively changing the color of hair, alkaline preparations are preferably used that are present in the form of an oil-in-water emulsion. On the one hand, this facilitates miscibility with the aqueous oxidation composition. On the other hand, the emulsified oil component and/or fatty component contribute(s) to nourishment of the fibers or the hair, and to improvement of the color result.

In addition, the alkaline preparations contain at least one alkalizing agent and optionally at least one oxidation dye precursor, and have a pH in the range of 8 to 11.5, measured at 20° C. Furthermore, alkaline preparations are preferably used which, in each case based on their weight, contain 50-80% by weight water, and also preferably 5-20% by weight, particularly preferably 8-15% by weight, of at least one fatty component having a melting point in the range of 28-80° C., which preferably is selected from linear saturated 1-alkanols having 12-30 carbon atoms, and esters of monohydric and polyhydric C1-C10 alkanols with C8-C30 alkanoic acids, and mixtures thereof, and in addition, preferably at least one nonionic and/or anionic surfactant in a total quantity of 1-8% by weight, preferably 2-6% by weight.

For oxidatively changing the color of the hair, the alkaline preparation is customarily mixed with an aqueous oxidizing agent preparation, for example in a reclosable bottle or a shaker, and the resulting cream-type application mixture is applied to the hair to be treated, where it remains for an exposure time of 5 to 60 minutes before being rinsed off.

In the development of such products, it is important to ensure that the application mixture has a sufficiently high viscosity with long-term stability, so that during the recommended exposure time it remains on the fibers or the hair, and does not prematurely lose viscosity or drip from the fibers or the hair. On the other hand, the particular initial viscosity of the oxidation composition and of the alkaline preparation should not be set too high, since otherwise it is difficult to produce a homogeneous, lump-free mixture from the two compositions.

Various potential solutions to this problem are already known in the prior art. For example, the acidic oxidation composition may contain higher quantities (for example, 1.5-5% by weight) of a (co)polymer of (meth)acrylic acid, (meth)acrylic acid esters, (meth)acrylic acid amides, or quaternized (meth)acrylic acid-based monomers, which undergoes greater thickening when mixed with the alkaline preparation under the influence of the increase in pH. Since very high pH values may occur locally during the mixing, inhomogeneities frequently arise in acrylate-thickened application mixtures; in turn, the inhomogeneous distribution of the dye adversely affects the color result. For alkaline preparations containing ammonia, the evaporation of the ammonia during the exposure time results in a lowering of the pH, as the result of which the application mixture loses viscosity, and in the most unfavorable case drips from the hair.

Another option for thickening the application mixture is to combine one composition (oxidation composition or alkaline composition) with an anionic surfactant, and to combine the other composition with a cationic surfactant. During mixing, the interaction between the two surfactants results in the desired increase in viscosity. However, not all users prefer the fairly pasty consistency of the application mixture that results. In addition, the cationic surfactant, in particular in the presence of hydrogen peroxide, may cause unpleasant irritation of the skin or the scalp.

The object of the present invention, therefore, is to provide an improved oxidizing agent preparation for oxidative color-changing agents that are present in the form of an oil-in-water emulsion and contain at least one alkalizing agent and optionally at least one oxidation dye precursor, and have a pH in the range of 8 to 11.5, measured at 20° C., with which homogeneous and viscosity-stable application mixtures may be prepared which during the entire exposure time have sufficient viscosity and remain on the hair without dripping off.

BRIEF SUMMARY OF THE INVENTION

A first subject matter of the present invention, therefore, is an oxidation composition for oxidative hair treatment, containing
  50-96% by weight, preferably 70-93% by weight, particularly preferably 80-90% by weight, water,
  0.5-20% by weight hydrogen peroxide,
  at least one polyethylene glycol ether of a monoester of glycerol and a C12-C22 carboxylic acid having 110-500 ethylene oxide units in the molecule, according to the following formula (I):

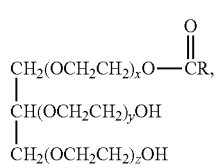

where the sum of the indices x+y+z stands for a number in the range of 110 to 500, and R stands for an alkyl functional group having 11 to 21 C atoms, and which may be saturated or unsaturated, linear or branched,
wherein all stated quantities are based on the weight of the oxidation composition.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

It has surprisingly been found that aqueous hydrogen peroxide preparations, including at least one polyethylene glycol ether of a monoester of glycerol and a C12-C22 carboxylic acid having 110-500 ethylene oxide units in the molecule, achieve the stated object very well.

The oxidation composition according to the invention includes 50-96% by weight, preferably 70-93% by weight, particularly preferably 80-90% by weight, water, in each case based on the weight of the oxidation composition.

The oxidation composition according to the invention includes 0.5-20% by weight, preferably 3-12% by weight, particularly preferably 6-9% by weight, hydrogen peroxide, in each case based on the weight of the oxidation composition.

The oxidation composition according to the invention includes at least one polyethylene glycol ether of a monoester of glycerol and a C12-C22 carboxylic acid having 110-500 ethylene oxide units in the molecule, according to the following formula (I):

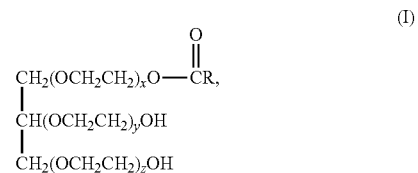

where the sum of the indices x+y+z stands for a number in the range of 110 to 500, and R stands for an alkyl functional group having 11 to 21 C atoms, and which may be saturated or unsaturated, linear or branched.

According to the invention, it is preferred that the polyethylene glycol ether according to formula (I) is selected from compounds for which the sum of the indices x+y+z stands for a number in the range of 120 to 450, preferably for a number in the range of 150 to 300, particularly preferably for a number in the range of 200 to 250.

The functional group RCO originates from a C12-C22 carboxylic acid which is preferably selected from lauric acid, myristic acid, palmitic acid, palmitoleic acid, stearic acid, isostearic acid, oleic acid, elaidic acid, petroselinic acid, linoleic acid, linolenic acid, arachidic acid, gadoleic acid, behenic acid, or erucic acid and the (technical) mixtures thereof.

Furthermore, it is preferred according to the invention that the polyethylene glycol ether according to formula (I) is selected from compounds for which R stands for a linear alkyl functional group having 15 to 17 C atoms, and which is preferably saturated. The functional group RCO preferably originates from palmitic acid or stearic acid and mixtures thereof.

Polyethylene glycol ethers according to formula (I) particularly preferred according to the invention are selected from PEG-200 glyceryl monopalmitate, PEG-200 glyceryl monostearate, PEG-200 glyceryl monolaurate, PEG-200 glyceryl monomyristate, PEG-120 glyceryl monopalmitate, PEG-120 glyceryl monostearate, PEG-120 glyceryl monolaurate, PEG-120 glyceryl monomyristate, PEG-150 glyceryl monopalmitate, PEG-150 glyceryl monostearate, PEG-150 glyceryl monolaurate, PEG-150 glyceryl monomyristate, PEG-300 glyceryl monopalmitate, PEG-300 glyceryl monostearate, PEG-300 glyceryl monolaurate, PEG-300 glyceryl monomyristate, and mixtures thereof. The ethoxylated glycerol may also be esterified with fatty acids and fatty acid mixtures originating from native oils, for example palm oil, palm kernel oil, coconut oil, sunflower oil, and other oils. One preferred example of such is PEG-200 glyceryl monopalmate. In addition, it may be preferred that the ethoxylated glycerol is esterified with hydrogenated fatty acids from native oils. One preferred example of such is PEG-200 Hydrogenated Glyceryl Palmate.

Oxidation compositions preferred according to the invention are characterized in that at least one polyethylene glycol ether according to formula (I) is included in a total quantity of 0.05 to 3% by weight, preferably 0.1 to 2% by weight, particularly preferably 0.2-0.7% by weight, in each case based on the weight of the oxidation composition. Further oxidation compositions preferred according to the invention are characterized in that at least one polyethylene glycol ether according to formula (I), selected from PEG-200 glyceryl monopalmitate, PEG-200 glyceryl monostearate, PEG-200 glyceryl monolaurate, PEG-200 glyceryl monomyristate, PEG-120 glyceryl monopalmitate, PEG-120 glyceryl monostearate, PEG-120 glyceryl monolaurate, PEG-120 glyceryl monomyristate, PEG-150 glyceryl monopalmitate, PEG-150 glyceryl monostearate, PEG-150 glyceryl monolaurate, PEG-150 glyceryl monomyristate, PEG-300 glyceryl monopalmitate, PEG-300 glyceryl monostearate, PEG-300 glyceryl monolaurate, PEG-300 glyceryl monomyristate, PEG-200 glyceryl monopalmate, PEG-200 Hydrogenated Glyceryl Palmate, and mixtures thereof, is included in a total quantity of 0.05 to 3% by weight, preferably 0.1 to 2% by weight, particularly preferably 0.2-0.7% by weight, in each case based on the weight of the oxidation composition. Oxidation compositions preferred according to the invention contain at least one polyethylene glycol ether according to formula (I), selected from PEG-200 glyceryl monopalmitate, PEG-200 glyceryl monostearate, PEG-120 glyceryl monopalmitate, PEG-120 glyceryl monostearate, PEG-150 glyceryl monopalmitate, PEG-150 glyceryl monostearate, PEG-300 glyceryl monopalmitate, PEG-300 glyceryl monostearate, PEG-200 glyceryl monopalmate, PEG-200 Hydrogenated Glyceryl Palmate, and mixtures thereof in a total quantity of 0.05 to 3% by weight, preferably 0.1 to 2% by weight, particularly preferably 0.2-0.7% by weight, in each case based on the weight of the oxidation composition. Oxidation compositions preferred according to the invention contain 0.05 to 3% by weight, preferably 0.1 to 2% by weight, particularly preferably 0.2-0.7% by weight, PEG-200 Hydrogenated Glyceryl Palmate, in each case based on the weight of the oxidation composition.

Oxidation compositions preferred according to the invention are characterized in that at least one polyethylene glycol ether of a monoester of glycerol and a C8-C22 carboxylic acid having 5-10 ethylene oxide units is included in the molecule, according to the following formula (II):

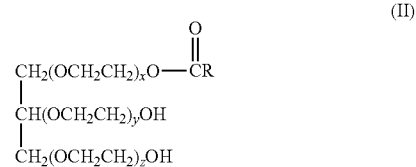

where the sum of the indices x+y+z stands for a number in the range of 5 to 10, and R stands for an alkyl functional group having 7 to 21 C atoms, and which may be saturated or unsaturated, linear or branched. According to the invention, it is particularly preferred that the polyethylene glycol ether according to formula (II) is selected from compounds for which the sum of the indices x+y+z stands for a number in the range of 5 to 10, preferably for a number in the range of 7 to 9, and R stands for a linear alkyl functional group having 7 to 17 C atoms and which is preferably saturated.

The functional group RCO originates from a C8-C22 carboxylic acid that is preferably selected from caproic acid, caprylic acid, capric acid, lauric acid, myristic acid, palmitic acid, palmitoleic acid, stearic acid, isostearic acid, oleic acid, elaidic acid, petroselinic acid, linoleic acid, linolenic acid, arachidic acid, gadoleic acid, behenic acid, or erucic acid, and the (technical) mixtures thereof.

Polyethylene glycol ethers according to formula (II) that are particularly preferred according to the invention are selected from PEG-7 glyceryl monolaurate, PEG-7 glyceryl monomyristate, PEG-7 glyceryl monopalmitate, PEG-7 glyceryl monostearate, PEG-7 glyceryl monocaprylate, PEG-7 glyceryl monocaprate, PEG-10 glyceryl monolaurate, PEG-10 glyceryl monomyristate, PEG-10 glyceryl monopalmitate, PEG-10 glyceryl monostearate, PEG-10 glyceryl monocaprylate, PEG-10 glyceryl monocaprate, PEG-5 glyceryl monolaurate, PEG-5 glyceryl monomyristate, PEG-5 glyceryl monopalmitate, PEG-5 glyceryl monostearate, PEG-5 glyceryl monocaprylate, PEG-5 glyceryl monocaprate, and mixtures thereof. The ethoxylated glycerol may also be esterified with fatty acids and fatty acid mixtures that originate from native oils, for example coconut oil, palm oil, palm kernel oil, sunflower oil, and other oils. One preferred example of such is PEG-7 glyceryl cocoate. In addition, it may be preferred that the ethoxylated glycerol is esterified with hydrogenated fatty acids from native oils.

Oxidation compositions preferred according to the invention are characterized in that at least one polyethylene glycol ether according to formula (II) is included in a total quantity of 0.03 to 3% by weight, preferably 0.05 to 2% by weight, particularly preferably 0.2-1.5% by weight, extremely preferably 0.5 to 1.0% by weight, in each case based on the weight of the oxidation composition.

Further oxidation compositions preferred according to the invention are characterized in that at least one polyethylene glycol ether according to formula (II), selected from PEG-7 glyceryl monolaurate, PEG-7 glyceryl monomyristate, PEG-7 glyceryl monopalmitate, PEG-7 glyceryl monostearate, PEG-7 glyceryl monocaprylate, PEG-7 glyceryl monocaprate, PEG-10 glyceryl monolaurate, PEG-10 glyceryl monomyristate, PEG-10 glyceryl monopalmitate, PEG-10 glyceryl monostearate, PEG-10 glyceryl monocaprylate, PEG-10 glyceryl monocaprate, PEG-5 glyceryl monolaurate, PEG-5 glyceryl monomyristate, PEG-5 glyceryl monopalmitate, PEG-5 glyceryl monostearate, PEG-5 glyceryl monocaprylate, PEG-5 glyceryl monocaprate, PEG-7 glyceryl cocoate, and mixtures thereof, preferably selected from PEG-7 glyceryl cocoate, is included in a total quantity of 0.03 to 3% by weight, preferably 0.05 to 2% by weight, particularly preferably 0.2-1.5% by weight, extremely preferably 0.5 to 1.0% by weight, in each case based on the weight of the oxidation composition, is included.

Further oxidation compositions preferred according to the invention are characterized in that at least one linear saturated 1-alkanol having 12-30 carbon atoms is included, preferably in a total quantity of 2.7-6% by weight, particularly preferably 3.0 to 5.0% by weight, in each case based on the weight of the oxidation composition.

The at least one linear saturated 1-alkanol having 12-30 carbon atoms is preferably selected from lauryl alcohol, myristyl alcohol, cetyl alcohol, stearyl alcohol, arachidyl alcohol, and behenyl alcohol and mixtures of these alkanols, and is particularly preferably selected from cetyl alcohol, stearyl alcohol, and cetyl alcohol/stearyl alcohol mixtures.

Preferred oxidation compositions according to the invention contain, in each case based on their weight, at least one linear saturated 1-alkanol having 12-30 carbon atoms in a total quantity of 2.7-6% by weight, preferably in a total quantity of 3.0-5.0% by weight, and contain at least one 1-alkanol selected from cetyl alcohol, stearyl alcohol, and cetyl alcohol/stearyl alcohol mixtures.

Further oxidation compositions preferred according to the invention are characterized in that they contain at least one polyethylene glycol ether of a linear saturated C12-C22 alkanol having 15-30 ethylene oxide units in the molecule.

It is preferred that at least one polyethylene glycol ether of a linear saturated C12-C22 alkanol having 15-30 ethylene oxide units is included in the molecule in a total quantity of 0.1-2% by weight, particularly preferably 0.5 to 5.0% by weight, in each case based on the weight of the oxidation composition.

The at least one polyethylene glycol ether is preferably selected from polyethylene glycol ethers of lauryl alcohol, myristyl alcohol, and cetyl alcohol, in each case having 15-30 ethylene oxide units in the molecule, and is particularly preferably selected from Ceteth-20, Steareth-20, Ceteareth-20, Ceteth-25, Steareth-25, Ceteareth-25, and mixtures thereof.

Further oxidation compositions preferred according to the invention are characterized in that at least one oil is included which is preferably selected from mineral oils and paraffin oils. It is preferred that at least one oil which is preferably selected from mineral oils and paraffin oils is included in a total quantity of 0.1-5% by weight, particularly preferably 0.2-3% by weight, extremely preferably 0.3-1% by weight, in each case based on the weight of the oxidation composition.

Oils preferred according to the invention are selected from natural and synthetic hydrocarbons, particularly preferably mineral oils, paraffin oils, $C_{18}$-$C_{30}$ isoparaffins, in particular isoeicosane, polyisobutene, and polydecene, which are available, for example, under the name Emery® 3004, 3006, 3010, or under the name Ethylflo® from Albemarle or Nexbase® 2004G from Nestle, and are also selected from $C_8$-$C_{16}$ isoparaffins, in particular isodecane, isododecane, isotetradecane, and isohexadecane and mixtures thereof, and 1,3-di-(2-ethylhexyl)cyclohexane (available, for example, under the trade name Cetiol® S from BASF).

Further oils preferred according to the invention are selected from the benzoic acid esters of linear or branched C8-22 alkanols. Particularly preferred are benzoic acid C12-C15 alkyl esters, available, for example, as the commercial product Finsolv® TN; benzoic acid isostearyl ester, available, for example, as the commercial product Finsolv® SB; ethylhexyl benzoate, available, for example, as the commercial product Finsolv® EB; and benzoic acid octyldocecyl ester, available, for example, as the commercial product Finsolv® BOD.

Further oils preferred according to the invention are selected from fatty alcohols having 6-30 carbon atoms, and which are unsaturated, or branched and saturated, or branched and unsaturated. The branched alcohols are often also referred to as Guerbet alcohols, since they are obtainable by the Guerbet reaction. Preferred alcohol oils are 2-hexyldecanol (Eutanol® G 16), 2-octyldodecanol (Eutanol® G), 2-ethylhexyl alcohol, and isostearyl alcohol.

Further preferred oils are selected from mixtures of Guerbet alcohols and Guerbet alcohol esters, for example the commercial product Cetiol® PGL (2-hexyldecanol and 2-hexyldecyl laurate).

Further cosmetic oils preferred according to the invention are selected from the triglycerides (triple esters of glycerol) of linear or branched, saturated or unsaturated, optionally hydroxylated C8-30 fatty acids. It may be particularly preferred to use natural oils, for example amaranth seed oil, apricot kernel oil, argan oil, avocado oil, babassu oil, cottonseed oil, borage seed oil, camelina oil, thistle oil, peanut oil, pomegranate seed oil, grapefruit seed oil, hemp oil, hazelnut oil, elderberry seed oil, black currant seed oil, jojoba oil, linseed oil, macadamia nut oil, corn germ oil, almond oil, marula oil, evening primrose oil, olive oil, palm oil, palm kernel oil, Brazil nut oil, pecan nut oil, peach kernel oil, rapeseed oil, castor oil, sea buckthorn pulp oil, sea buckthorn seed oil, sesame oil, soybean oil, sunflower oil, grapeseed oil, walnut oil, wild rose oil, wheat germ oil, and the liquid components of coconut oil and the like. However, synthetic triglyceride oils, in particular capric/caprylic triglycerides, for example the commercial products Myritol® 318, Myritol® 331 (BASF), or Miglyol® 812 (Hüls) having unbranched fatty acid functional groups, and glyceryl tri-isostearin having branched fatty acid functional groups, are also preferred.

Further cosmetic oils particularly preferred according to the invention are selected from the dicarboxylic acid esters of linear or branched C2-C10 alkanols, in particular diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Further cosmetic oils particularly preferred according to the invention are selected from the esters of linear or branched, saturated or unsaturated fatty alcohols having 2-30 carbon atoms with linear or branched, saturated or unsaturated fatty acids having 2-30 carbon atoms, and which may be hydroxylated. These include 2-hexyldecyl stearate (Eutanol® G 16 S), 2-hexyldecyl laurate, isodecyl neopentanoate, isononyl isononanoate, 2-ethylhexyl palmitate (Cegesoft® C 24), and 2-ethylhexyl stearate (Cetiol® 868). Likewise preferred are isopropyl myristate, isopropyl palmitate, isopropyl stearate, isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyl octanoate, diisotridecyl acetate, n-butyl stearate, n-hexyl laurate, n-decyl oleate, oleyl oleate, oleyl erucate, erucyl oleate, erucyl erucate, ethylene glycol dioleate, and ethylene glycol dipalmitate.

Further cosmetic oils preferred according to the invention are selected from the addition products of 1 to 5 propylene oxide units with monohydric or polyhydric C8-22 alkanols such as octanol, decanol, decanediol, lauryl alcohol, myristyl alcohol, and stearyl alcohol, for example PPG-2 myristyl ether and PPG-3 myristyl ether (Witconol® APM).

Further cosmetic oils preferred according to the invention are selected from the addition products of at least 6 ethylene oxide and/or propylene oxide units with monohydric or polyhydric C3-22 alkanols such as glycerol, butanol, butanediol, myristyl alcohol, and stearyl alcohol, which may be esterified if desired, for example PPG-14 butyl ether (Ucon Fluid®AP), PPG-9 butyl ether (Breox® B25), PPG-10 butanediol (Macol® 57), PPG-15 stearyl ether (Arlamol® E), and glycereth-7-diisononanoate.

Further cosmetic oils preferred according to the invention are selected from the C8-C22 fatty alcohol esters of monohydric or polyhydric C2-C7 hydroxycarboxylic acids, in particular the esters of glycolic acid, lactic acid, malic acid, tartaric acid, citric acid, and salicylic acid. Such esters based on linear C14/15 alkanols, for example C12-C15 alkyl lactate, and based on C12/13 alkanols branched in the 2-position, are obtainable under the trademark Cosmacol® from Nordmann, Rassmann GmbH & Co, Hamburg, in particular the commercial products Cosmacol® ESI, Cosmacol® EMI, and Cosmacol® ETI.

Further cosmetic oils preferred according to the invention are selected from the symmetrical, asymmetrical, or cyclic esters of carbonic acid with $C_{3-22}$ alkanols, $C_{3-22}$ alkane diols, or $C_{3-22}$ alkane triols, for example dicaprylyl carbonate (Cetiol® CC) or the esters according to the teaching of DE 19756454 A1, in particular glycerol carbonate.

Further cosmetic oils that may be preferred according to the invention are selected from the esters of dimers of unsaturated $C_{12}$-$C_{22}$ fatty acids (dimer fatty acids) with monohydric linear, branched, or cyclic $C_2$-$C_{18}$ alkanols or with polyhydric linear or branched $C_2$-$C_6$ alkanols.

Further cosmetic oils that are suitable according to the invention are selected from silicone oils, including, for example, dialkyl and alkylaryl siloxanes such as cyclopentasiloxane, cyclohexasiloxane, dimethyl polysiloxane, and methyl phenyl polysiloxane, as well as hexamethyl disiloxane, octamethyl trisiloxane, and decamethyl tetrasiloxane. Volatile silicone oils, which may be cyclic, such as octamethyl cyclotetrasiloxane, decamethyl cyclopentasiloxane, and dodecamethyl cyclohexasiloxane, and mixtures thereof, as included, for example, in the commercial products DC 244, 245, 344, and 345 from Dow Corning, may be preferred. Also suitable are volatile linear silicone oils, in particular hexamethyl disiloxane ($L_2$), octamethyl trisiloxane ($L_3$), decamethyl tetrasiloxane ($L_4$), as well as any given binary and ternary mixtures of $L_2$, $L_3$, and/or $L_4$, preferably mixtures that are included, for example, in the commercial products DC 2-1184, Dow Corning® 200 (0.65 cSt) and Dow Corning® 200 (1.5 cSt) from Dow Corning. Preferred nonvolatile silicone oils are selected from higher-molecular linear dimethyl polysiloxanes, commercially available, for example, under the names Dow Corning® 190 and Dow Corning® 200 Fluid, having kinematic viscosities (25° C.) in the range of 5-100 cSt, preferably 5-50 cSt, or also 5-10 cSt, and dimethyl polysiloxane, having a kinematic viscosity (25° C.) of approximately 350 cSt.

It may be extremely preferred according to the invention to use mixtures of the above-mentioned oils.

The oxidation composition according to the invention preferably has a viscosity in the range of 1500-3500 mPas, particularly preferably 2000-3000 mPas, in each case measured at 20° C. in a Haake Model MV2 viscometer at a speed of 8 rpm.

For stabilizing the oxidizing agent during storage, it is particularly preferred when the oxidation composition according to the invention has an acidic pH, in particular a pH in the range of 2.5 to 5.5, preferably 3.0 to 5.0. Preferred acidifiers are edible acids, for example citric acid, acetic acid, malic acid, or tartaric acid, and diluted mineral acids, in particular phosphoric acid.

For stabilizing the oxidizing agent in the oxidation composition according to the invention, it is preferred to use so-called complexing agents. Complexing agents are substances that are able to complex metal ions. Preferred complexing agents are so-called chelate complexing agents, i.e., substances that form cyclic compounds with metal ions, whereby an individual ligand occupies more than one coordination site on a central atom. The number of bound ligands depends on the coordination number of the central ion. Examples of customary chelate complexing agents preferred within the scope of the present invention are polyoxycarboxylic acids, polyamines, ethylenediaminetetraacetic acid (EDTA), nitrilotriacetic acid (NTA), and hydroxyethane diphosphonic acids and the alkali salts thereof. Complexing agents preferred according to the invention are phosphonates, preferably hydroxyalkane or aminoalkane phosphonates, and in particular 1-hydroxyethane-1,1-diphosphonate (HEDP) or the di- or tetrasodium salt thereof, and/or ethylenediaminetetramethylene phosphonate (EDTMP) or the hexasodium salt thereof, and/or diethylenetriamine pentamethylene phosphonate (DTPMP) or the hepta- or octasodium salt thereof. Dipicolinic acid is also preferably used according to the invention as a complexing agent. Agents including a combination of an EDTA salt and HEDP and dipicolinic acid are particularly preferred according to the invention.

Further oxidation compositions preferred according to the invention are summarized below, wherein all stated quantities are based on the weight of the oxidation composition:
- 50-96% by weight, preferably 70-93% by weight, particularly preferably 80-90% by weight, water,
- 0.5-20% by weight hydrogen peroxide,
- in a total quantity of 0.05-3% by weight, at least one polyethylene glycol ether of a monoester of glycerol and a C12-C22 carboxylic acid having 110-500 ethylene oxide units in the molecule, according to the following formula (I):

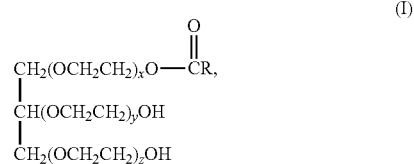

where the sum of the indices x+y+z stands for a number in the range of 110 to 500, and R stands for an alkyl functional group having 11 to 21 C atoms, and which may be saturated or unsaturated, linear or branched,
including 0.05-3% by weight PEG-200 Hydrogenated Glyceryl Palmate,
wherein all stated quantities are based on the weight of the oxidation composition;

50-96% by weight, preferably 70-93% by weight, particularly preferably 80-90% by weight, water,
0.5-20% by weight hydrogen peroxide,
in a total quantity of 0.05-3% by weight, at least one polyethylene glycol ether of a monoester of glycerol and a C12-C22 carboxylic acid having 110-500 ethylene oxide units in the molecule, according to the following formula (I):

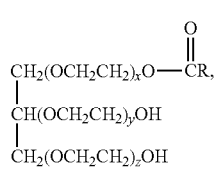
(I)

where the sum of the indices x+y+z stands for a number in the range of 110 to 500, and R stands for an alkyl functional group having 11 to 21 C atoms, and which may be saturated or unsaturated, linear or branched,
in a total quantity of 0.03-3% by weight, at least one polyethylene glycol ether of a monoester of glycerol and a C8-C22 carboxylic acid having 5-10 ethylene oxide units in the molecule, according to the following formula (II):

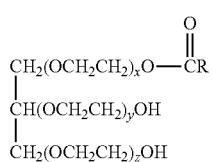
(II)

where the sum of the indices x+y+z stands for a number in the range of 5 to 10, and R stands for an alkyl functional group having 7 to 21 C atoms, and which may be saturated or unsaturated, linear or branched,
including 0.05-3% by weight PEG-200 Hydrogenated Glyceryl Palmate and 0.03-3% by weight PEG-7 Glyceryl Cocoate,
wherein all stated quantities are based on the weight of the oxidation composition;
50-96% by weight, preferably 70-93% by weight, particularly preferably 80-90% by weight, water,
0.5-20% by weight hydrogen peroxide,
in a total quantity of 0.05-3% by weight, at least one polyethylene glycol ether of a monoester of glycerol and a C12-C22 carboxylic acid having 110-500 ethylene oxide units in the molecule, according to the following formula (I):

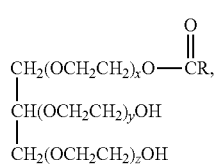
(I)

where the sum of the indices x+y+z stands for a number in the range of 110 to 500, and R stands for an alkyl functional group having 11 to 21 C atoms, and which may be saturated or unsaturated, linear or branched,
in a total quantity of 0.03-3% by weight, at least one polyethylene glycol ether of a monoester of glycerol and a C8-C22 carboxylic acid having 5-10 ethylene oxide units in the molecule, according to the following formula (II):

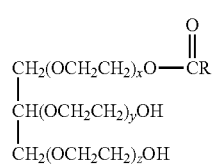
(II)

where the sum of the indices x+y+z stands for a number in the range of 5 to 10, and R stands for an alkyl functional group having 7 to 21 C atoms, and which may be saturated or unsaturated, linear or branched,
at least one linear saturated 1-alkanol having 12-30 carbon atoms in a total quantity of 2.7-6% by weight, particularly preferably 3.0 to 5.0% by weight,
including 0.05-3% by weight PEG-200 Hydrogenated Glyceryl Palmate and 0.03-3% by weight PEG-7 Glyceryl Cocoate and 2.7-6% by weight cetearyl alcohol,
wherein all stated quantities are based on the weight of the oxidation composition;
50-96% by weight, preferably 70-93% by weight, particularly preferably 80-90% by weight, water,
0.5-20% by weight hydrogen peroxide,
in a total quantity of 0.05-3% by weight, at least one polyethylene glycol ether of a monoester of glycerol and a C12-C22 carboxylic acid having 110-500 ethylene oxide units in the molecule, according to the following formula (I):

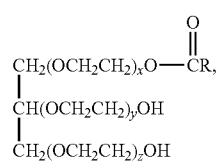
(I)

where the sum of the indices x+y+z stands for a number in the range of 110 to 500, and R stands for an alkyl functional group having 11 to 21 C atoms, and which may be saturated or unsaturated, linear or branched,
in a total quantity of 0.03-3% by weight, at least one polyethylene glycol ether of a monoester of glycerol and a C8-C22 carboxylic acid having 5-10 ethylene oxide units in the molecule, according to the following formula (II):

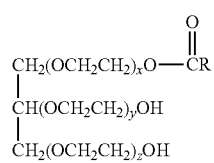
(II)

where the sum of the indices x+y+z stands for a number in the range of 5 to 10, and R stands for an alkyl functional group having 7 to 21 C atoms, and which may be saturated or unsaturated, linear or branched, at least one linear saturated 1-alkanol having 12-30 carbon atoms in a total quantity of 2.7-6% by weight, particularly preferably 3.0 to 5.0% by weight, at least one polyethylene glycol ether of a linear saturated C12-C22 alkanol having 15-30 ethylene oxide units in the molecule in a total quantity of 0.1-2% by weight, particularly preferably 0.5 to 5.0% by weight, including 0.05-3% by weight PEG-200 Hydrogenated Glyceryl Palmate and 0.03-3% by weight PEG-7 Glyceryl Cocoate and 2.7-6% by weight cetearyl alcohol and 0.1-2% by weight Ceteareth-20, wherein all stated quantities are based on the weight of the oxidation composition;

50-96% by weight, preferably 70-93% by weight, particularly preferably 80-90% by weight, water, 0.5-20% by weight hydrogen peroxide, in a total quantity of 0.05-3% by weight, at least one polyethylene glycol ether of a monoester of glycerol and a C12-C22 carboxylic acid having 110-500 ethylene oxide units in the molecule, according to the following formula (I):

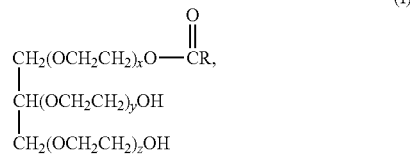

where the sum of the indices x+y+z stands for a number in the range of 110 to 500, and R stands for an alkyl functional group having 11 to 21 C atoms, and which may be saturated or unsaturated, linear or branched, in a total quantity of 0.03-3% by weight, at least one polyethylene glycol ether of a monoester of glycerol and a C8-C22 carboxylic acid having 5-10 ethylene oxide units in the molecule, according to the following formula (II):

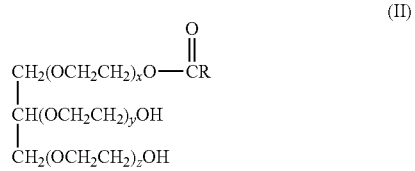

where the sum of the indices x+y+z stands for a number in the range of 5 to 10, and R stands for an alkyl functional group having 7 to 21 C atoms, and which may be saturated or unsaturated, linear or branched, at least one linear saturated 1-alkanol having 12-30 carbon atoms in a total quantity of 2.7-6% by weight, particularly preferably 3.0 to 5.0% by weight, at least one polyethylene glycol ether of a linear saturated C12-C22 alkanol having 15-30 ethylene oxide units in the molecule in a total quantity of 0.1-2% by weight, particularly preferably 0.5 to 5.0% by weight, at least one oil, which is preferably selected from mineral oils and paraffin oils, in a total quantity of 0.1-5% by weight, particularly preferably 0.2-3% by weight, extremely preferably 0.3-1% by weight, including 0.05-3% by weight PEG-200 Hydrogenated Glyceryl Palmate and 0.03-3% by weight PEG-7 Glyceryl Cocoate and 2.7-6% by weight cetearyl alcohol and 0.1-2% by weight Ceteareth-20 and 0.3-1% by weight paraffin oil, wherein all stated quantities are based on the weight of the oxidation composition.

A further subject matter of the present patent invention relates to a kit for oxidatively changing the color of keratinic fibers, containing two separate compositions (A) and (B), wherein composition (B) is an oxidation composition according to the invention or preferred according to the invention, as described above, i.e., an oxidation composition containing 50-96% by weight, preferably 70-93% by weight, particularly preferably 80-90% by weight, water, 0.5-20% by weight hydrogen peroxide, at least one polyethylene glycol ether of a monoester of glycerol and a C12-C22 carboxylic acid having 110-500 ethylene oxide units in the molecule, according to the following formula (I):

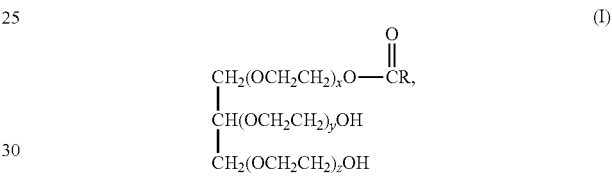

where the sum of the indices x+y+z stands for a number in the range of 110 to 500, and R stands for an alkyl functional group having 11 to 21 C atoms, and which may be saturated or unsaturated, linear or branched, wherein all stated quantities are based on the weight of the oxidation composition; and composition (A) is present in the form of an oil-in-water emulsion and includes at least one alkalizing agent and optionally at least one oxidation dye precursor, and has a pH in the range of 8 to 11.5, measured at 20° C., wherein compositions (A) and (B) are preferably present in a weight ratio (A)/(B) in the range of 0.33-3, particularly preferably 0.5-2, extremely preferably 1:1.

Composition (A) corresponds to the alkaline preparation described above.

Composition (A) includes at least one alkalizing agent selected from the group comprising ammonia, alkanolamines, basic amino acids, and inorganic alkalizing agents such as (alkaline earth)/alkali metal hydroxides, (alkaline earth)/alkali metal metasilicates, (alkaline earth)/alkali metal phosphates, and (alkaline earth)/alkali metal hydrogen phosphates. Suitable inorganic alkalizing agents are sodium hydroxide, potassium hydroxide, sodium silicate, and sodium metasilicate. Organic alkalizing agents that are usable according to the invention are selected from monoethanolamine, 2-amino-2-methylpropanol, and triethanolamine. The basic amino acids usable as alkalizing agent according to the invention are preferably selected from the group comprising arginine, lysine, ornithine, and histidine, particularly preferably arginine.

Composition (A) includes at least one alkalizing agent that is preferably selected from ammonia and monoethanolamine, and mixtures of these alkalizing agents.

Ammonia ($NH_3$) is usually used in the form of its aqueous solution. Aqueous ammonia solutions often contain ammonia ($NH_3$) in concentrations of 10 to 32% by weight. Use of an aqueous ammonia solution including 25% by weight ammonia ($NH_3$) is preferred. The total quantity of alkalizing agents is preferably selected in such a way that the mixture, i.e., the ready-to-apply color-changing agent, has an alkaline pH, preferably a pH of 8 to 11.5, particularly preferably a pH of 8.5 to 11, extremely preferably a pH of 9.0 to 10.5. Ammonia and/or monoethanolamine are/is preferably included in composition (A) used according to the invention in quantities of 0.01-10% by weight, preferably 0.1 to 7.5% by weight, more preferably 0.2 to 5.5% by weight, and particularly preferably 0.4 to 4.5% by weight, in each case based on the weight of composition (A), so that the pH of composition (A) is in the range of 8 to 11.5, measured at 20° C.

As an optional ingredient, the emulsion-type alkaline composition (A) used according to the invention includes at least one oxidation dye precursor, which is preferably selected from one or more developer components and optionally one or more coupler components.

At least one oxidation dye precursor is preferably included in a total quantity of 0.0001 to 10.0% by weight, preferably 0.001 to 8% by weight, in each case based on the weight of composition (A).

It may be preferred according to the invention to select as developer component at least one compound from the group comprising p-phenylenediamine, p-toluylenediamine, 2-(2-hydroxyethyl)-p-phenylenediamine, 2-(1,2-dihydroxyethyl)-p-phenylenediamine, N,N-bis-(2-hydroxyethyl)-p-phenylenediamine, N-(4-amino-3-methylphenyl)-N-[3-(1H-imidazol-1-yl)propyl]amine, N,N-bis-(2-hydroxyethyl)-N, N-bis-(4-aminophenyl)-1,3-diaminopropan-2-ol, bis-(2-hydroxy-5-aminophenyl)methane, 1,3-bis-(2,5-diaminophenoxy)propan-2-ol, N,N'-bis-(4-aminophenyl)-1, 4-diazacycloheptane, 1,10-bis-(2,5-diaminophenyl)-1,4,7, 10-tetraoxadecane, p-aminophenol, 4-amino-3-methylphenol, 4-amino-2-aminomethylphenol, 4-amino-2-(1,2-dihydroxyethyl)phenol, 4-amino-2-(diethylaminomethyl)phenol, 4,5-diamino-1-(2-hydroxyethyl)pyrazole, 2,4,5,6-tetraaminopyrimidine, 4-hydroxy-2,5,6-triaminopyrimidine, 2-hydroxy-4,5,6-triaminopyrimidine, and the physiologically acceptable salts thereof.

At least one developer component is preferably included in a total quantity of 0.0001 to 10.0% by weight, preferably 0.001 to 8% by weight, in each case based on the weight of composition (A).

Within the scope of oxidative dyeing, coupler components alone do not provide significant coloration; rather, they always require the presence of developer components. Therefore, the additional use of at least one coupler component is preferred according to the invention when at least one developer component is used.

Coupler components preferred according to the invention are selected from 3-aminophenol, 5-amino-2-methylphenol, N-cyclopentyl-3-aminophenol, 3-amino-2-chloro-6-methylphenol, 2-hydroxy-4-aminophenoxyethanol, 2,6-dimethyl-3-aminophenol, 3-trifluoroacetylamino-2-chloro-6-methylphenol, 5-amino-4-chloro-2-methylphenol, 5-amino-4-methoxy-2-methylphenol, 5-(2-hydroxyethyl)amino-2-methylphenol, 3-(diethylamino)phenol, N-cyclopentyl-3-aminophenol, 1,3-dihydroxy-5-(methylamino)benzene, 3-ethylamino-4-methylphenol, 2,4-dichloro-3-aminophenol, 2-(2,4-diaminophenoxy)ethanol, 1,3-bis-(2,4-diaminophenoxy)propane, 1-methoxy-2-amino-4-(2-hydroxyethylamino)benzene, 1,3-bis-(2,4-diaminophenyl)propane, 2,6-bis-(2'-hydroxyethylamino)-1-methylbenzene, 2-({3-[(2-hydroxyethyl)amino]-4-methoxy-5-methylphenyl}amino) ethanol, 2-({3-[(2-hydroxyethyl)amino]-2-methoxy-5-methylphenyl}amino)ethanol, 2-({3-[(2-hydroxyethyl) amino]-4,5-dimethylphenyl}amino)ethanol, 2-[3-morpholin-4-ylphenyl)amino]ethanol, 3-amino-4-(2-methoxyethoxy)-5-methylphenylamine, 1-amino-3-bis-(2-hydroxyethyl)aminobenzene, resorcinol, resorcinol monomethyl ether, 2-methylresorcinol, 5-methylresorcinol, 2,5-dimethylresorcinol, 2-chlororesorcinol, 4-chlororesorcinol, pyrogallol, 1,2,4-trihydroxybenzene, 2,6-dihydroxypyridine, 2-amino-3-hydroxypyridine, 2-amino-5-chloro-3-hydroxypyridine, 3-amino-2-methylamino-6-methoxypyridine, 2,6-dihydroxy-3,4-dimethylpyridine, 2,6-dihydroxy-4-methylpyridine, 2,6-diaminopyridine, 2,3-diamino-6-methoxypyridine, 3,5-diamino-2,6-dimethoxypyridine, 2,6-dihydroxy-3,4-dimethylpyridine, 3,4-diaminopyridine, 2-(2-methoxyethyl)amino-3-amino-6-methoxypyridine, 2-(4'-methoxyphenyl)amino-3-aminopyridine, 1-naphthol, 2-methyl-1-naphthol, 2-hydroxymethyl-1-naphthol, 2-hydroxyethyl-1-naphthol, 1,3-dihydroxynaphthalene, 1,5-dihydroxynaphthalene, 1,6-dihydroxynaphthalene, 1,7-dihydroxynaphthalene, 1,8-dihydroxynaphthalene, 2,7-dihydroxynaphthalene, 2,3-dihydroxynaphthalene, 4-hydroxyindole, 6-hydroxyindole, 7-hydroxyindole, 4-hydroxyindoline, 6-hydroxyindoline, 7-hydroxyindoline, 4,6-diaminopyrimidine, 4-amino-2,6-dihydroxypyrimidine, 2,4-diamino-6-hydroxypyrimidine, 2,4, 6-trihydroxypyrimidine, 2-amino-4-methylpyrimidine, 2-amino-4-hydroxy-6-methylpyrimidine, and 4,6-dihydroxy-2-methylpyrimidine, or mixtures of these compounds or the physiologically acceptable salts thereof.

At least one coupler component is preferably included in a total quantity of 0.0001 to 10.0% by weight, preferably 0.001 to 8% by weight, in each case based on the weight of composition (A).

Developer components and coupler components are generally used in approximately equimolar quantities with respect to one another. If equimolar use has also proven to be appropriate, a certain excess of individual oxidation dye precursors is not disadvantageous, so that developer components and coupler components may be included in a molar ratio of 1:0.5 to 1:3, in particular 1:1 to 1:2.

Kits preferred according to the invention for oxidatively changing the color of keratinic fibers are characterized in that the above-mentioned oxidation composition (B) according to the invention or preferred according to the invention and the above-mentioned emulsion-type alkaline composition (A) are included in a weight ratio A/B of 0.33 to 3, particularly preferably 0.5 to 2, and extremely preferably in a weight ratio of 1:1.

Kits particularly preferred according to the invention for oxidatively changing the color of keratinic fibers are characterized in that the above-mentioned oxidation composition (B) according to the invention or preferred according to the invention and the above-mentioned emulsion-type alkaline composition (A) are included in a weight ratio A/B of 0.33 to 3, particularly preferably 0.5 to 2, and extremely preferably in a weight ratio of 1:1; the kit includes no further components that are added to the ready-to-apply color-changing mixture, while components for pretreating or aftertreating the keratinic fibers, for example conditioners or shampoos, may be included in the kit.

In one embodiment that is preferred according to the invention, the kit according to the invention is characterized in that composition (A), in each case based on its weight, includes 50-80% by weight water, and also 5-20% by weight, preferably 8-15% by weight, of at least one fatty component having a melting point in the range of 28-80° C., and which is preferably selected from linear saturated 1-alkanols having 12-30 carbon atoms, and esters of monohydric and polyhydric C1-C10 alkanols and C8-C30 alkanoic acids and mixtures thereof, and also at least one nonionic and/or anionic surfactant in a total quantity of 1-8% by weight, preferably 2-6% by weight.

Suitable fatty components having a melting point in the range of 28-80° C. are selected, for example, from esters of a saturated monohydric $C_{16}$-$C_{60}$ alkanol and a saturated $C_8$-$C_{36}$ monocarboxylic acid, in particular cetyl behenate, stearyl behenate, and $C_{20}$-$C_{40}$ alkyl stearate, glycerol triesters of saturated linear $C_{12}$-$C_{30}$ carboxylic acids, which may be hydroxylated, candelilla wax, carnauba wax, beeswax, saturated linear $C_{14}$-$C_{36}$ carboxylic acids, and also coco fatty acid glycerol mono-, di-, and triesters, Butyrospermum parkii (shea butter), and esters of saturated monohydric $C_8$-$C_{18}$ alcohols with saturated $C_{12}$-$C_{18}$ monocarboxylic acids, for example stearyl laurate, cetearyl stearate, cetyl palmitate, and myristyl myristate, and also the above-mentioned linear saturated 1-alkanols having 12-30 carbon atoms, in particular lauryl alcohol, myristyl alcohol, cetyl alcohol, stearyl alcohol, arachidyl alcohol, and behenyl alcohol, and also glyceryl monostearate, glyceryl distearate, glyceryl monocaprinate, glyceryl monocaprylate, glyceryl monolaurate, glyceryl monomyristate, glyceryl monopalmitate, glyceryl monohydroxy stearate, glyceryl monooleate, glyceryl monolanolate, glyceryl dimyristate, glyceryl dipalmitate, glyceryl dioleate, propylene glycol monostearate, propylene glycol monolaurate, sorbitan monocaprylate, sorbitan monolaurate, sorbitan monomyristate, sorbitan monopalmitate, sorbitan monostearate, sorbitan sesquistearate, sorbitan distearate, sorbitan dioleate, sorbitan sesquioleate, sucrose distearate, diglycerol monostearate, diglycerol monoisostearate, diglycerol monooleate, diglycerol dihydroxystearate, diglycerol distearate, diglycerol dioleate, triglycerol distearate, tetraglycerol monostearate, tetraglycerol distearate, tetraglycerol tristearate, decaglycerol pentastearate, decaglycerol pentahydroxystearate, decaglycerol pentaisostearate, decaglycerol pentaoleate, and mixtures of the above-mentioned substances.

Examples of suitable nonionic surfactants are alkylene oxide addition products of fatty alcohols and fatty acids with 2 to 50 moles ethylene oxide per mole of fatty alcohol or fatty acid in each case, as well as alkyl or alkenyl oligoglycosides, for example decyl glucoside.

Examples of suitable anionic surfactants are fatty acids, alkyl sulfates, alkyl ether sulfates, and ethercarboxylic acids having 10 to 20 C atoms in the alkyl group and up to 16 glycol ether groups in the molecule.

The statements concerning the oxidation compositions according to the invention and preferred according to the invention and the emulsion-type alkaline compositions (A) used according to the invention apply mutatis mutandis with regard to further preferred embodiments of the kit according to the invention.

A further subject matter of the present patent invention relates to a method for oxidatively changing the color of keratinic fibers, characterized by the following method steps:

Providing an oxidation composition (B) according to one of claims 1 to 11, including 50-96% by weight, preferably 70-93% by weight, particularly preferably 80-90% by weight, water,
0.5-20% by weight hydrogen peroxide, at least one polyethylene glycol ether of a monoester of glycerol and a C12-C22 carboxylic acid having 110-500 ethylene oxide units in the molecule, according to the following formula (I):

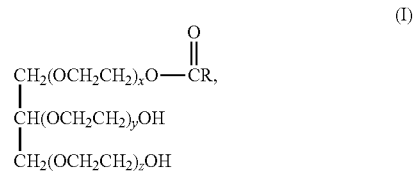

where the sum of the indices x+y+z stands for a number in the range of 110 to 500, and R stands for an alkyl functional group having 11 to 21 C atoms, and which may be saturated or unsaturated, linear or branched, wherein all stated quantities are based on the weight of the oxidation composition, and Providing a composition (A) which is present in the form of an oil-in-water emulsion and includes at least one alkalizing agent and optionally at least one oxidation dye precursor, and has a pH in the range of 8 to 11.5, measured at 20° C., and also preferably includes, in each case based on its weight, 50-80% by weight water, also preferably 5-20% by weight, particularly preferably 8-15% by weight, of at least one fatty component having a melting point in the range of 28-80° C., and which is preferably selected from linear saturated 1-alkanols having 12-30 carbon atoms, and esters of monohydric and polyhydric C1-C10 alkanols and C8-C30 alkanoic acids and mixtures thereof, and preferably at least one nonionic and/or anionic surfactant in a total quantity of 1-8% by weight, preferably 2-6% by weight, preparing a mixture of the above-mentioned oxidation composition (B) and the above-mentioned composition (A), preferably in a weight-based mixture ratio (A)/(B) in the range of 0.33-3, particularly preferably 0.5-2, extremely preferably 1:1, and immediately afterwards distributing the ready-to-apply agent on the fibers, retaining of the agent on the fibers for a period of 1 to 60 minutes, immediately followed by rinsing out the remaining agent from the fibers and optionally drying the fibers.

Methods preferred according to the invention for oxidatively changing the color of keratinic fibers are characterized in that the above-mentioned oxidation composition (B) and the above-mentioned emulsion-type alkaline composition (A) are mixed together in a weight-based mixture ratio (A)/(B) in the range of 0.33-3, particularly preferably 0.5-2, extremely preferably 1:1.

Further embodiments according to the invention of the oxidation composition, the kit, and the dyeing method are characterized in that oxidation composition (B) as well as composition (A) contain cationic surfactants, polysaccharides, and (co)polymers of (meth)acrylic acid, (meth)acrylic acid esters, (meth)acrylic acid amides, or quaternized (meth)acrylic acid-based monomers in a total quantity of 0 to 0.5% by weight, preferably 0.05 to 0.3% by weight, particularly preferably 0.08 to 0.2% by weight, in each case based on the weight of the individual composition (A) or (B).

In certain cases, it has proven to be unfavorable for the application properties and also for the skin tolerability properties of the ready-to-apply color-changing agent, when compositions (A) and/or (B) contain(s) more than 0.5% by weight of cationic surfactants, polysaccharides, and (co)

polymers of (meth)acrylic acid, (meth)acrylic acid esters, (meth)acrylic acid amides, or quaternized (meth)acrylic acid-based monomers.

The statements concerning the oxidation compositions according to the invention and preferred according to the invention and the emulsion-type alkaline compositions (A) used according to the invention apply mutatis mutandis with regard to further preferred embodiments of the method according to the invention.

According to the invention, keratinic or keratin-containing fibers are understood to mean wool, fur, feathers, and in particular human hair. In principle, however, the dyeing and/or lightening methods according to the invention may also be used for application to other natural fibers, for example cotton, jute, sisal, linen, silk, or modified natural fibers, for example regenerated cellulose, nitrocellulose, alkylcellulose, hydroxyalkylcellulose, or acetylcellulose.

The ready-to-apply coloring agent of the method according to the invention is preferably prepared by combining the oxidation composition according to the invention or preferred according to the invention with an emulsion-type alkaline composition (A) used according to the invention in a reclosable container, and subsequent mixing. The ready-to-apply coloring agent is distributed on the keratinic fibers in the subsequent method step. In the method for changing the color of human hair, the ready-to-apply agent is distributed directly on the hair on the user's head. The distribution preferably takes place manually. For this purpose, the user removes the ready-to-apply agent from the mixture container, preferably the reclosable container, by drawing or pouring onto the hand, followed by distributing and preferably working the agent into the hair on the head. Direct contact between the ready-to-apply color-changing agent and the hands is preferably avoided by using suitable gloves, such as disposable gloves made of latex, for example.

The ready-to-apply coloring agent subsequently remains on the fibers to be treated for a period of 1 to 60 min. The time period is preferably in the range of 10 to 45 min, particularly preferably 20 to 30 min.

The application temperatures may be in a range between 15 and 40° C. During the retention time of the agent on the fibers, a higher or precisely defined temperature may also optionally be set by external heat sources. It is particularly preferred to assist the color-changing operation using physical measures. Methods according to the invention in which the application is assisted during the exposure time by the action of heat, IR radiation, and/or UV radiation may be preferred.

After the exposure time elapses, the ready-to-apply coloring agent or the remaining coloring agent in the last method step is removed by rinsing it out of the fibers to be treated. For this purpose, the fibers are rinsed with water and/or an aqueous surfactant preparation. Warm water at a temperature of 20° C. to 40° C. or an appropriately heat-controlled aqueous surfactant preparation is typically used for this purpose. This may optionally be followed by further treatment steps, such as applying a leave-on or rinse-off conditioner, an additional dyeing step, for example the coloring or lightening of hair strands, hair shaping, and/or drying the hair.

EXAMPLES

The following preparations were prepared. Table 1 includes an example of an O/W emulsion-type alkaline composition (A); Table 2 includes an example of an oxidation composition (B) according to the invention. Unless stated otherwise, the stated quantities are in % by weight, in each case based on the weight of the individual composition.

TABLE 1

| Emulsion-type (O/W) alkaline composition (A) (dye preparation) | |
| --- | --- |
| Cetearyl alcohol | 13.0 |
| Ammonium hydroxide | 6.4 |
| Glyceryl stearate | 3.5 |
| Monoethanolamine | 1.0 |
| Ceteareth-20 | 3.5 |
| Octyldodecanol | 2.0 |
| Sodium laureth sulfate | 0.9 |
| Sodium cetearyl sulfate | 0.5 |
| Serine | 0.5 |
| Fragrance | 0.5 |
| Oleic acid | 0.3 |
| Silica | 0.25 |
| Potassium stearate | 0.5 |
| Titanium dioxide | 0.7 |
| Glycerol | 1.5 |
| Tetrasodium EDTA | 0.2 |
| Toluene-2,5-diamine sulfate | 0.15 |
| Sodium sulfite | 0.15 |
| Carbomer | 0.2 |
| Keratin hydrolysate | 0.1 |
| Potassium hydroxide | 0.06 |
| Resorcinol | 0.06 |
| Ascorbic acid | 0.05 |
| Linoleamidopropyl PG-Dimonium Chloride Phosphate | 0.1 |
| Propylene glycol | 1.0 |
| 2-Amino-4-hydroxyethylaminoanisole sulfate | 0.01 |
| m-Aminophenol | 0.01 |
| Water | To make 100 |

TABLE 2

| Oxidation compositions (B) according to the invention | | |
| --- | --- | --- |
| 2,6-Dicarboxypyridine | 0.1 | 0.1 |
| Sodium benzoate | 0.04 | 0.04 |
| Disodium pyrophosphate | 0.1 | 0.1 |
| Etidronic acid | 0.15 | 0.15 |
| Potassium hydroxide | 0.095 | 0.095 |
| Cetearyl alcohol | 3.4 | 3.4 |
| Ceteareth-20 | 1 | 1 |
| Paraffinum liquidum (mineral oil) | 0.3 | 0.3 |
| PEG-7 Glyceryl Cocoate | 0.1 | 1.0 |
| PEG-200 Hydrogenated Glyceryl | 0.4 | 0.2 |
| Hydrogen peroxide | 6.0 | 6.0 |
| Water | To make 100 | To make 100 |

Coloration 100 g of the dye preparation was mixed with 100 g of the oxidation composition according to the invention by vigorous, continuous shaking (40 times) in a reclosable mixing container.

The products were scooped out by hand from the containers in each case and uniformly distributed on two identical hair strands (Alkino).

The respective ready-to-apply agent remained on the hair strands for an exposure period of 30 min at room temperature (20° C.) without dripping off.

The remaining agent was subsequently rinsed out of the hair strands with lukewarm water (25° C.) for approximately 2 min, and the strands were dried with a towel. Uniform, durable, and glossy colorings having high intensity and vividness of color were obtained.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An oxidation composition for oxidative hair treatment, comprising:
    50-96% by weight water,
    0.5-20% by weight hydrogen peroxide,
    at least one polyethylene glycol ether of a monoester of glycerol and a C12-C22 carboxylic acid having 110-500 ethylene oxide units in the molecule, according to the following formula (I):

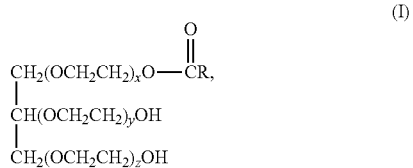

where the sum of the indices x+y+z stands for a number in the range of 110 to 500, and R stands for an alkyl functional group having 11 to 21 C atoms, and which may be saturated or unsaturated, linear or branched,
    in a total quantity of 0.03-3% by weight, at least one polyethylene glycol ether of a monoester of glycerol and a C8-C22 carboxylic acid having 5-10 ethylene oxide units in the molecule, according to the following formula (II):

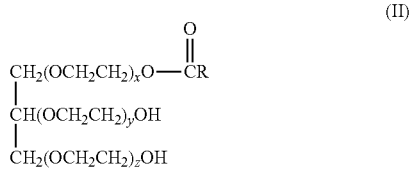

where the sum of the indices x+y+z stands for a number in the range of 5 to 10, and R stands for an alkyl functional group having 7 to 21 C atoms, and which may be saturated or unsaturated, linear or branched,
    2.7-6% by weight of at least one linear saturated 1-alkanol having 12-30 carbon atoms,
    0.1-2% by weight of at least one polyethylene glycol ether of a linear saturated C12-C22 alkanol having 15-30 ethylene oxide units in the molecule,
    0.1-5% by weight of at least one oil selected from the group of mineral oils and paraffin oils, and mixtures thereof
wherein all stated quantities are based on the weight of the oxidation composition.

2. The composition according to claim 1, wherein the water comprises 80-90% by weight of the oxidative hair treatment.

3. The composition according to claim 1, wherein the polyethylene glycol ether according to formula (I) is selected from compounds for which the sum of the indices x+y+z is in the range of 120 to 450.

4. The composition according to claim 1, wherein the polyethylene glycol ether according to formula (I) is selected from compounds for which the sum of the indices x+y+z is in the range of 200 to 250.

5. The composition according to claim 1, wherein the polyethylene glycol ether according to formula (I) is selected from compounds for which R stands for a linear alkyl functional group having 15 to 17 C atoms.

6. The composition according to claim 1, wherein the polyethylene glycol ether according to formula (I) wherein the polyethylene glycol ether according to formula (I) is selected from PEG-200 glyceryl monopalmitate, PEG-200 glyceryl monostearate, PEG-120 glyceryl monopalmitate, PEG-120 glyceryl monostearate, PEG-150 glyceryl monopalmitate, PEG-150 glyceryl monostearate, PEG-300 glyceryl monopalmitate, PEG-300 glyceryl monostearate, PEG-200 glyceryl monopalmitate, PEG-200 Hydrogenated Glyceryl Palmate, and mixtures thereof.

7. The composition according to claim 1, wherein the polyethylene glycol ether according to formula (I) is PEG-200 Hydrogenated Glyceryl Palmate.

8. The composition according to claim 1, wherein the at least one polyethylene glycol ether according to formula (I) is included in a total quantity of 0.05 to 3% by weight, based on the total weight of the oxidation composition.

9. The composition according to claim 1, wherein the polyethylene glycol ether according to formula (II) is selected from the group consisting of: PEG-7 glyceryl monolaurate, PEG-7 glyceryl monomyristate, PEG-7 glyceryl monopalmitate, PEG-7 glyceryl monostearate, PEG-7 glyceryl monocaprylate, PEG-7 glyceryl monocaprate, PEG-10 glyceryl monolaurate, PEG-10 glyceryl monomyristate, PEG-10 glyceryl monopalmitate, PEG-10 glyceryl monostearate, PEG-10 glyceryl monocaprylate, PEG-10 glyceryl monocaprate, PEG-5 glyceryl monolaurate, PEG-5 glyceryl monomyristate, PEG-5 glyceryl monopalmitate, PEG-5 glyceryl monostearate, PEG-5 glyceryl monocaprylate, PEG-5 glyceryl monocaprate, PEG-7 glyceryl cocoate, and mixtures thereof.

10. The composition accord to claim 1, wherein the polyethylene glycol ether of formula (II) is PEG-7 glyceryl cocoate.

11. The composition according to claim 1, wherein the composition has a pH of 2.5 to 5.5 and a viscosity of 1500 to 3500 mPas measured at 20° C.

12. A kit for oxidatively changing the color of keratinic fibers, comprising:
    two separate compositions (A) and (B),
    wherein composition (B) is an oxidation composition according to claim 1 and composition (A) is present in the form of an oil-in-water emulsion and includes at least one alkalizing agent and optionally at least one oxidation dye precursor and has a pH in the range of 8 to 11.5, measured at 20° C., wherein compositions (A) and (B) are present in a weight ratio (A)/(B) in the range of 0.33-3.

13. A method for oxidatively changing the color of keratinic fibers, comprising:
    providing an oxidation composition (B) according to claim 1, comprising
    providing a composition (A) which is present in the form of an oil-in-water emulsion and includes at least one alkalizing agent and optionally at least one oxidation dye precursor, and has a pH in the range of 8 to 11.5, measured at 20° C., in each case based on its weight, 50-80% by weight water, 5-20% by weight of at least one fatty component having a melting point in the range of 28–80° C., and esters of monohydric and polyhydric C1-C10 alkanols and C8-C30 alkanoic acids, and mixtures thereof, and
preparing a mixture of the above-mentioned oxidation composition (B) and the above-mentioned composition (A) in a weight-based mixture ratio (A)/(B) in the range of 0.33-3 and immediately afterwards distributing the ready-to-apply agent on the fibers, maintaining the agent on the fibers for a period of 1 to 60 minutes, immediately followed by rinsing out the remaining agent from the fibers and optionally drying the fibers.

\* \* \* \* \*